United States Patent [19]

Boyer

[11] Patent Number: 4,979,811

[45] Date of Patent: Dec. 25, 1990

[54] EYELID COVER

[76] Inventor: Wesley E. Boyer, 1055 W. Baseline #2006, Mesa, Ariz. 85210

[21] Appl. No.: 482,308

[22] Filed: Feb. 20, 1990

[51] Int. Cl.$^5$ .............................. G02C 7/10; A61E 9/00
[52] U.S. Cl. ............................................ 351/44; 2/15; 128/858
[58] Field of Search ................... 351/44, 47; 2/11, 15, 2/431; 128/858

[56] References Cited

U.S. PATENT DOCUMENTS

| | | | |
|---|---|---|---|
| 3,020,552 | 2/1962 | Coon | 2/15 |
| 4,642,816 | 2/1987 | Miller | 2/15 |
| 4,701,962 | 10/1987 | Simon | 2/15 |

Primary Examiner—Paul M. Dzierzynski
Attorney, Agent, or Firm—Richard R. Mybeck

[57] ABSTRACT

A flexible eyelid cover pre-formed for secure placement in a eyesocket over the eyelid with only a single wetting and without the use of adhesive. The cover is formed of closed cell thermoplastic UV barrier material having a plurality of suction-cup like dimples disposed on the rear surface thereof and which upon initial wetting, conforms to the shape of the eyelid and adheres thereto. A frontal layer of nylon is provided to support a decorative design thereon.

5 Claims, 1 Drawing Sheet

EYELID COVER

The present invention relates generally to an eye protective device and more particularly to an improved self-retained shielding device for protecting one's eyes and eyelids from the adverse effects of solar radiation during sun bathing.

BACKGROUND OF THE INVENTION

The present invention relates to eyelid covers, and more particularly to improved means for protecting the human eye from the adverse effects of direct solar radiation such as is encountered during sun bathing and like activities.

A number of eyelid protecting covers have been previously proposed for use by sunbathers. Among such previously known protectors, none of which proved to be wholly satisfactory in use, are Loos (I) in U.S. Pat. No. 2,527,947 who disclosed an eye protector comprising a flexible pad or shield formed of fabric or like material which, only after continuous saturation with eye lotion, water or the like, will adhere to the closed eyelid and conform to the shape of the eye. Loos (II), in U.S. Pat. No. 2,572,638, a continuation-in-part of Loos I, described an inner layer of velour which is added to the basic structure having a water proof plastic central portion and a sun-intercepting outer layer. Constant saturation with fluids is again required to maintain attachment of the shield to the eye and the conformity of the shape of the shield to the eye.

Another prior art approach described by Bowman in U.S. Pat. No. 3,068,863, involves the use of the traditional "pirate" eyepatch which is attached to the face and covers the entire eye socket. Bowman was particularly remembered for the raccoon-like eye appearance it provided its user.

Towner Jr., in U.S. Pat. No. 3,619,815, Stover in U.S. Pat. No. 4,559,746 and Heltman in U.S. Pat. No. 4,682,371 taught other variants of eye patches, each of which required adhesive strips to hold the patch in place.

Each of the foregoing suffered from inherent disadvantages. For instance, those devices which were soley dependent on liquid surface tension for adherence lost their integrity when the fluid either dried or evaporated and was not replaced. Others required a porous material and constant wetness to maintain its eye conforming shape while still others created unnatural and somewhat embarrassing "raccoon like" tanning patterns on the user's face. Still others required the use of sticky, inherently uncomfortable and potentially toxic adhesives in engagement either with the eyelid or the face adjacent the eye and were not capable of reuse.

Accordingly, a need still exists for a preformable eyelid protective device which will remain in situ during extended periods of exposure to the sun, which will create a tanning pattern which is consistant with and compliments the natural topography of the face, which will avoid the use of adhesives which are not only uncomfortable to "wear" but pose a possible danger to the eye itself by introducing an alien substance thereinto, and which can be used repeatedly without loss of effectiveness. It is toward the provision of an eyelid cover which overcomes the prior art deficiencies and meets the aforestated needs that the present invention is directed.

BRIEF SUMMARY OF THE INVENTION

The present invention provides an eyelid protector which overcomes the above-mentioned disadvantages of the prior art devices in a novel and unique fashion.

More particularly, the present invention comprises a strategically pre-formed body member having an outer layer and a porous inner layer intergrally formed therewith. Thus formed, the body member has a convex outer surface and a concave inner surface. Body member is further provided with a convex upper edge, and essentially straight lower edge. The body is dimensioned so that the back surface intimately approaches and/or contacts the wearer's closed eyelid, while the upper edge of the body is disposed in close proximity to and above the eye, adjacent the upper rim of the optic socket. The lower edge is disposed in close proximity to and below the eyeball and adjacent to the lower eyelash line.

The body of the device is of substantially uniform thickness throughout and the inner layer thereof is formed of an opaque ultraviolet ("UV") absorbent and reflective closed cell material having elastic memory. Suitable dimpled cavities are defined in rear surface of the inner layer to create a mini suction cup effect which cooperates to maintain the device in its desired position on the wearer's eyelid. The outer layer of the device is preferably composed of an opaque material.

Accordingly, it is a prime object of the present invention to provide a new and improved eyelid cover which overcomes the disadvantages of the prior art devices.

Another object of the present invention is to provide a new and improved pre-formed eyelid cover which by coaction of its elastic memory and strategically disposed suction cups is able to be set within and remain so positioned relative to the eye socket and protect the eye and eyelid from harmful solar radiation.

These and still further objects as shall hereinafter appear are fulfilled by the present invention in a remarkably unexpected fashion as can be readily discerned from the following detailed description of a preferred embodiment thereof, especially when read in conjunction with the accompanying drawing in which like parts bear like numerals throughout the several views.

BRIEF DESCRIPTION OF THE INVENTION

DESCRIPTION OF THE PREFERRED EMBODIMENTS

Figure 1:
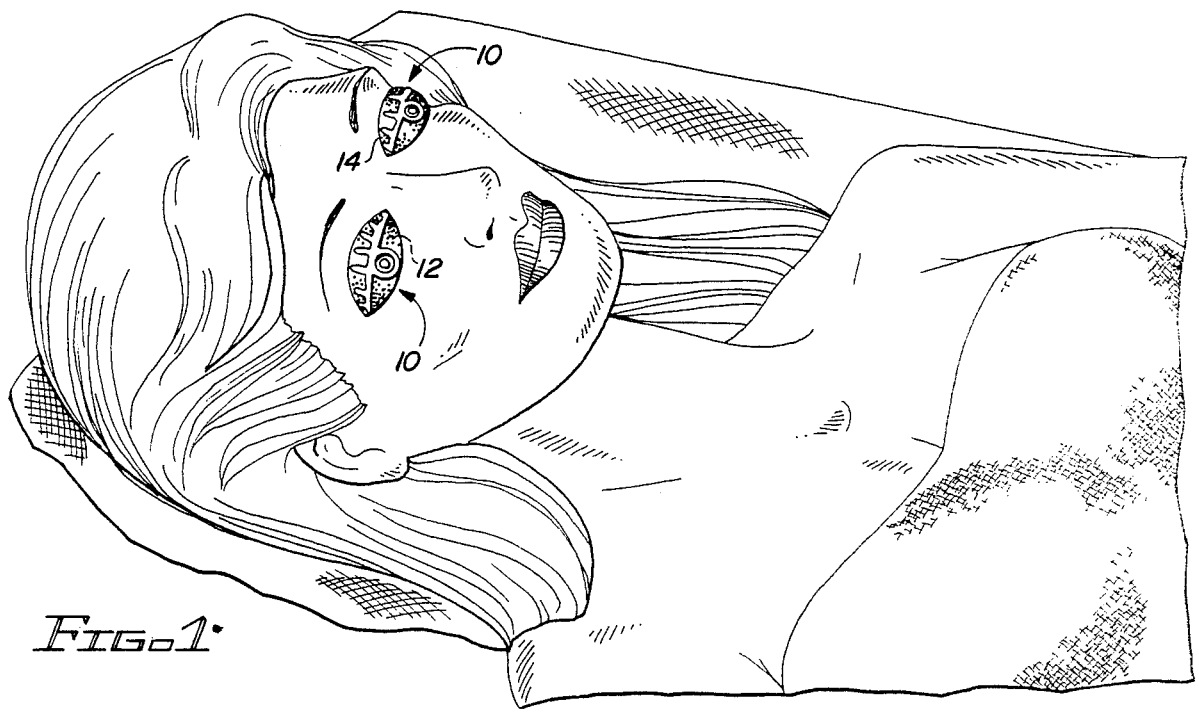
FIG. 1 is an isometric view of a sun bather using the device embodying the present invention.
Figure 2:
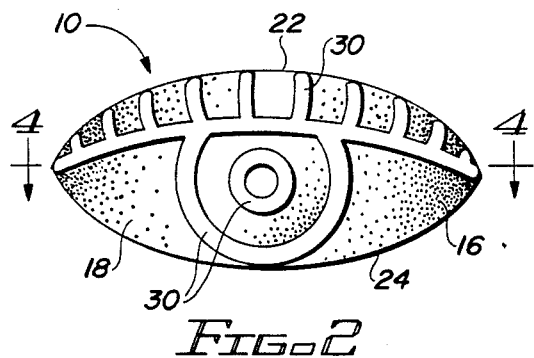
FIG. 2 is front elevation of an eyelid cover embodying the present invention.
Figure 3:
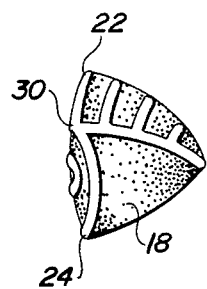
FIG. 3 is a side view of the eyelid cover of FIG. 2.

Referring to the drawing by reference numbers, the device embodying the present invention is identified the general numeral 10. The device 10, as shown in FIG. 1, is disposed one over each of the wearer's eyes 12, and resides in suction-induced spring-biased locked engagement within the socket 14 surrounding each eye.

As shown in FIGS. 2-5, each device 10 comprises a body portion 16 having a frontal layer 18, a rear layer 20, each extending between an upper edge 22 and a lower edge 24. As is clearly shown in FIG. 4, frontal layer 18 is convex, while the rear layer 20 is concave. Upper edge 22 is curvilinearly convex while lower edge 24 is essentially horizontal between two upwardly curving end portions.

The concavity set into rear layer 20 is in substantial conformity with the contour of the human eyeball. In preferred practice, each device 10 has an overall thickness of approximately 3–4 mm and the concavity of rear layer 20 normally will provide an offset of approximately 1–2 mm between the center of the surface of device 10 and the ends thereon. As will appear, the concavity of device 10 in concert with the dimpled cavities 28 defined in layer 20 coacts to maintaining device 10 in operative position on eyelid associated with eye 12 in socket 14.

Figure 4:
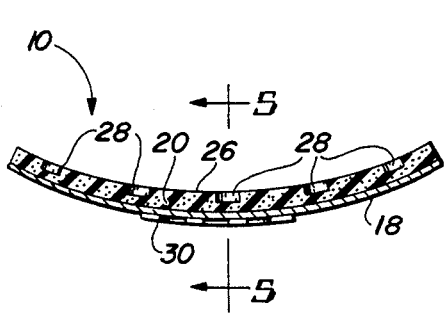
FIG. 4 is a cross-section taken along line 4—4 of FIG. 2.
Figure 5:
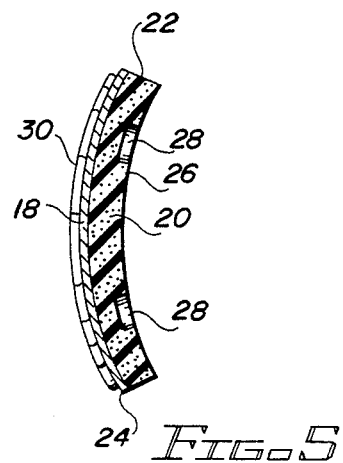
FIG. 5 is a cross-section taken along line 5—5 of FIG. 4.

As shown in FIG. 4, device 10 comprises a rear or inner layer 20 and a frontal or outer layer 18 which layers are bonded together in surface-to-surface engagement in any suitable manner such as by flame bonding. Inner layer 20 of device 10 is fabricated from a closed cell material which not only is ultraviolet ("UV") reflective and absorbent, also opaque and possesses shape retaining memory. A particularly suitable material for use in the practice of this invention is expanded closed cell ethyl vinyl acetate. Outer layer 18 is bonded to inner layer 20 and may be provided with a decorative design 30 if desired.

Dimpled cavities 28 are defined in rear surface 26 by the application of a heated pin directly into inner layer 20. The heated pin displaces the plastic material from which layer 20 is formed to define dimpled cup or cavity 28 which, as formed, is impervious to the flow of water therethrough and thus provides an effective suction cup for device 10.

In use, device 10 is initially wetted sufficiently to soak inner layer 20 and each dimpled cavity 28. The wetted device 10 is then gently inserted into the wearer's eye socket 14 over the eyelid whereupon the concavity of device 10, the suction created by cavities 28 and the surface tension provided by wet rear layer 20 causes the device 10 to be secured and maintained in its desired location. With wetted device 10 disposed over an eyelid, the device 10 remains in place until physically removed by the wearer because the water does not evaporate therefrom. Bottom surface 20 remains in essentially intimate contact with the surface of the closed eyelid of eye 12, while the upper edge 22 and lower edge 24 of device 10 complement the natural contour of eye socket 14.

The frontal layer 18 is preferably formed of nylon cloth which in addition to being attractive is effective to hold and retain a colorful painted design thereupon.

Expanded closed-cell ethyl vinyl acetate is the preferred material for rear layer 20 as it provides not only a cushioned form-fit, but is sufficiently pliant to assume and maintain a precise preshaping of the device to conform to the contour of the eyelid. Furthermore, closed cell ethyl vinyl acetate is both exceedingly durable and readily washable and thus provides a device which can be used from season to season. Further the use of a closed-cell material such as ethyl vinyl acetate prevents the entrainment of bacteria and other foreign materials and allows the formation of the small dimpled suction-cups 28 in the rear surface thereof, cups 28 being essentially water tight and resistant to the passage of water and other foreign substance therethrough. The ultraviolet absorbancy of ethyl vinyl acetate further protects the eye from damage which could result from UV radiation on the eye.

In use, device 10 enables the user to obtain facial tanning without the raccoon-looking tan lines created by sunglasses, eye patches and the like devices. Further, by shielding the eye from ultraviolet radiation, a highly suspect cause of cataracts is eliminated. Further, the device herein described and illustrated needs to be positioned only once during extending tanning sessions and avoids the constant rewetting and repositioning required by prior art devices.

The device herein described enables the wearers to gain the ultimate in facial tanning while providing eye protection and comfort with a perfect alternative to chemically based sun screens. It should be noted that while the use of sun screens and UV blockers is important, many contain nitros-amines which opthamologists do not recommend for use in or near the human eyes.

The several displaced dimples, when moistened with water, coact with the elastic memory of the device to create a gentle suction which allows the device to conform and adhere to the user's eyelid. Because of the unique closed-cell structure of the layer abutting the eye, a thin layer of moisture is maintained to hold the cover in place until it is deliberately removed.

From the foregoing, it becomes apparent that new and useful procedures have been herein described and illustrated which fulfill all of the aforestated objectives in a remarkably unexpected fashion. It is of course understood that such modifications, alterations and adaptations as may readily occur to an artisan having the ordinary skills to which this invention pertains are intended within the spirit of the present invention which is limited only by the scope of the claims appended hereto.

Accordingly what is claimed is:

1. An eyelid covering device mountable within a human eye socket over an eyelid comprising: a preformed durable non-porous body portion having a convex frontal surface and a concave rear surface, a plurality of suction-cup like dimples defined in said rear surface in spaced relationship to each other, said body portion being capable of receiving and retaining a single wetting, said wetted body portion coacting with said dimples to maintain said body portion in said eye socket over said eyelid.

2. A device according to claim 1 in which is body portion comprises an outer layer and an inner layer integrally secured to each other in surface-to-surface engagement therewith.

3. A device according to claim 2 in which said outer layer is nylon.

4. A device according to claim 2 in which said inner layer is expanded closed cell ethyl vinyl acetate.

5. A device according to claim 3 in which said inner layer is expanded closed cell ethyl vinyl acetate.

* * * * *